United States Patent
Wolter

(10) Patent No.: US 10,772,484 B2
(45) Date of Patent: Sep. 15, 2020

(54) PUMP DEVICE

(71) Applicant: OLYMPUS WINTER & IBE GMBH, Hamburg (DE)

(72) Inventor: Michael Wolter, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 32 days.

(21) Appl. No.: 15/119,228

(22) PCT Filed: Mar. 6, 2015

(86) PCT No.: PCT/EP2015/054755
§ 371 (c)(1),
(2) Date: Aug. 16, 2016

(87) PCT Pub. No.: WO2015/139972
PCT Pub. Date: Sep. 24, 2015

(65) Prior Publication Data
US 2017/0007099 A1    Jan. 12, 2017

(30) Foreign Application Priority Data
Mar. 18, 2014   (DE) ......................... 10 2014 204 997

(51) Int. Cl.
*A61B 1/00* (2006.01)
*A61B 1/015* (2006.01)
(Continued)

(52) U.S. Cl.
CPC ...... *A61B 1/00055* (2013.01); *A61B 1/00045* (2013.01); *A61B 1/00165* (2013.01);
(Continued)

(58) Field of Classification Search
CPC ....... A61B 1/0125; A61B 1/015; A61B 1/125; A61B 1/00043; A61B 1/00055;
(Continued)

(56) References Cited

U.S. PATENT DOCUMENTS 4,416,268 A * 11/1983 Hagino .............. A61B 1/00119
600/132
4,813,400 A * 3/1989 Washizuka ......... A61B 1/00165
385/117
(Continued)

FOREIGN PATENT DOCUMENTS

CN          202876062 U      4/2013
WO       2013/160443 A1    10/2013

OTHER PUBLICATIONS

Jun. 5, 2015 International Search Report issued in International Patent Application No. PCT/EP2015/054755.
(Continued)

*Primary Examiner* — Ryan N Henderson
*Assistant Examiner* — Pamela F Wu
(74) *Attorney, Agent, or Firm* — Oliff PLC

(57) ABSTRACT

A pump device for use in operating theatres and to arrangements composed of corresponding pump devices and endoscopes. A pump device according to the invention for use in operating theatres includes a pump unit with a pump and a control unit, and a pump hose attached to the pump unit. The pump unit further includes a light source that can be controlled by the control unit to display the operating state of the pump unit. The pump hose has a fibre optic which extends along the pump hose, wherein the first end of the fibre optic is designed to couple in light from the controllable light source. The arrangement according to the invention includes a pump device according to the invention and an endoscope, which is designed to deliver flushing liquid to the operating site.

10 Claims, 4 Drawing Sheets

(51) Int. Cl.
*A61B 1/07* (2006.01)
*A61B 1/12* (2006.01)

(52) U.S. Cl.
CPC ............. *A61B 1/015* (2013.01); *A61B 1/07* (2013.01); *A61B 1/12* (2013.01)

(58) Field of Classification Search
CPC ........... A61B 1/00071; A61B 1/00096; A61B 1/00112; A61B 1/00121; A61B 1/00126; A61B 1/00147; A61B 1/00154; A61B 1/00163; A61B 1/00165; A61B 1/00167; A61B 1/0017; A61B 1/06; A61B 1/0607; A61B 1/0605; A61B 1/0615; A61B 1/0661; A61B 1/0669; A61B 1/07; A61B 1/12; A61B 1/126; A61B 1/128
USPC .................................. 600/117–118, 156, 158
See application file for complete search history.

(56) References Cited

U.S. PATENT DOCUMENTS

| | | | |
|---|---|---|---|
| 2003/0216617 A1* | 11/2003 | Hirakui | A61B 1/015 600/159 |
| 2006/0030751 A1* | 2/2006 | Uesugi | A61B 1/00068 600/101 |
| 2012/0176769 A1* | 7/2012 | Reimer | A61B 3/0008 362/84 |
| 2013/0338436 A1* | 12/2013 | Dresher | A61B 1/06 600/109 |
| 2014/0066839 A1* | 3/2014 | Torisawa | A61M 13/003 604/26 |

OTHER PUBLICATIONS

Sep. 29, 2016 International Preliminary Report on Patentability issued in International Patent Application No. PCT/EP2015/054755.

* cited by examiner

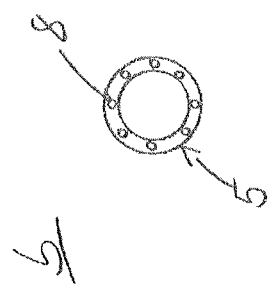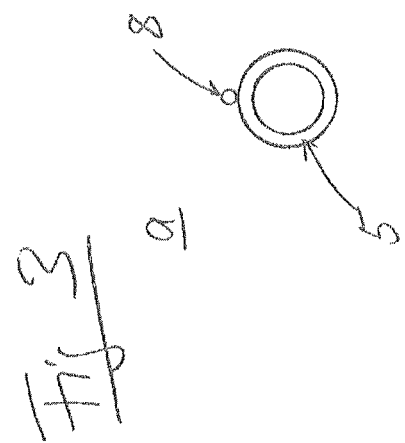

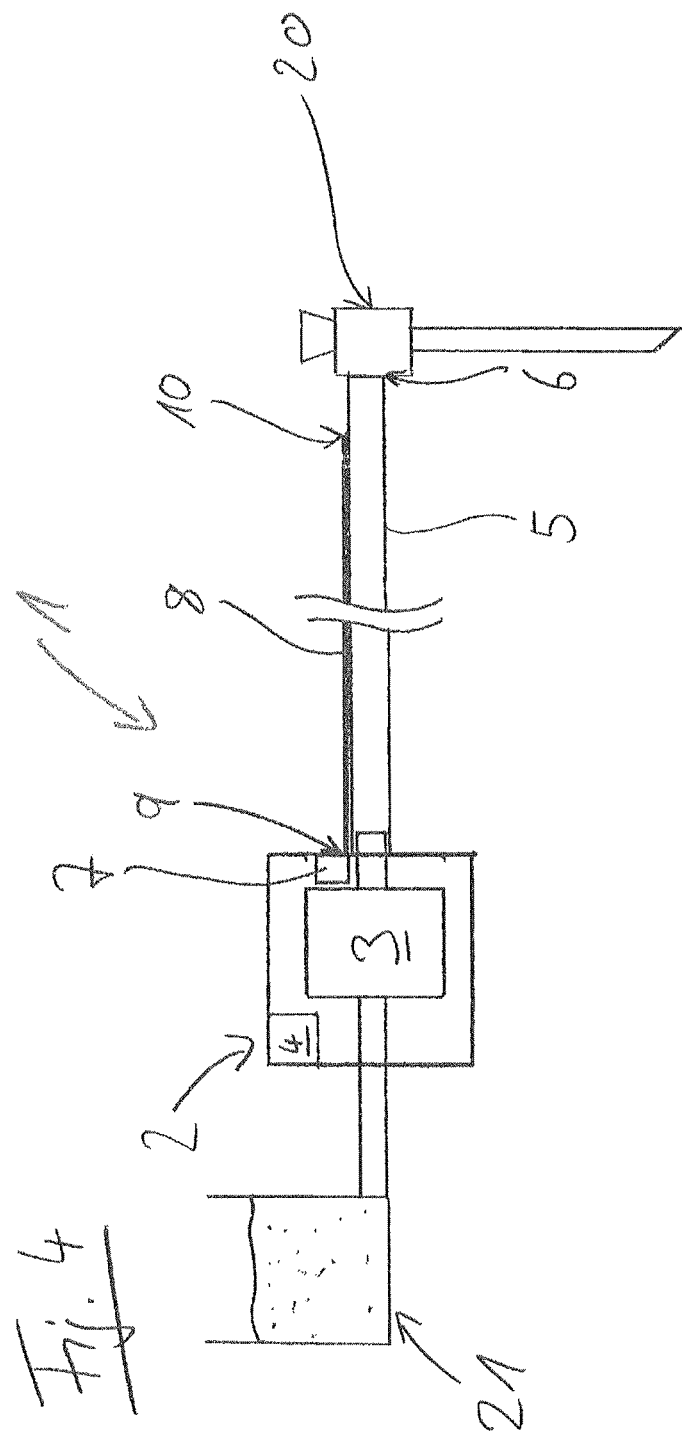

PUMP DEVICE

The invention relates to pump devices for use in operating theaters, and arrangements made of corresponding pump devices and endoscopes.

Pumps are often found in the field of medical engineering for operating theaters as parts of medical instruments or as separate units connected to medical instruments. Examples hereof include suction pumps or heart-lung machines. Pumps are also used for supplying rinsing liquids into an operating region, by means of which resected tissue and blood can be washed out of the operating region.

In the field of minimally invasive surgery, it is known to introduce rinsing liquid into the operating region or into a body cavity comprising the operating region with the aid of a pump. In so doing, the body cavity is filled and widened by the rinsing liquid in such a way that the operating region is readily visible to the surgeon through an endoscope. Here, the rinsing liquid is regularly supplied and, optionally, also removed again by means of the endoscope itself. Furthermore, a continuous rinsing liquid flow can avoid clouding over of the field of view as a result of suspended solids or the like. Moreover, resected tissue and blood can be washed out.

Corresponding pumps according to the prior art, which are used in operating theaters, supply information about the operating state thereof, such as e.g. the basic switched-on state of the pump or the flow rate, by way of a display arranged on the housing thereof. In general, the housing of the pump or the display arranged thereon is not in the field of view of the surgeon, and so he needs to turn toward the pump during the operation in an appropriate manner or ask the persons assisting with the operation about the operating state of the pump in order to obtain the information indicated on the display. This prior art is disadvantageous as the concentration of the surgeon in respect of the actual operation is interrupted in both aforementioned cases.

The invention is therefore based on the object of developing a pump which no longer has the disadvantages of the prior art, or at least only has these to a reduced extent.

This object is achieved by a pump device in accordance with the main claim and by an arrangement in accordance with claim 10. Advantageous developments are the subject matter of the dependent claims.

According thereto, the invention relates to a pump device for use in operating theaters, comprising a pump unit with a pump and a control unit, and a pump tube connected to the pump unit, wherein the pump unit comprises a light source actuatable by the control unit to display the operating state of the pump unit and the pump tube has an optical fiber extending along the pump tube, wherein the first end of the optical fiber is arranged for coupling-in light from the actuatable light source.

The invention furthermore relates to an arrangement made of a pump device according to the invention and an endoscope, which is embodied to supply rinsing liquid into the operating region, wherein the free end of the pump tube of the pump device according to the invention is connected to the endoscope for supplying rinsing liquid.

By virtue of an optical fiber, into which light from a light source reflecting the operating state of the pump unit is coupled-in, extending along the pump tube being provided according to the invention, it is possible to display the information about the operating state of the pump unit in the direct vicinity of the operating region such that a surgeon can perceive the corresponding information practically in passing, without his concentration for the actual operation being disturbed in the process. Here, the invention makes use of the circumstance that the free end of the pump tube of a pump device for use in operating theaters is regularly introduced into the actual operating region, or into the vicinity thereof, as a result of which the optical fiber extending along the pump tube, which is provided according to the invention, is also guided into the direct vicinity of the operating region. At the second end of the optical fiber, the light coupled-in at the first end reemerges and it is visible to the surgeon as a point of light. As a result of the actuation of the light source according to the invention, this point of light supplies the surgeon with information about the operating state of the pump.

The second end of the optical fiber can be arranged at the end of the pump tube. In this case, the second end of the optical fiber is preferably arranged in a region at a distance of between 0 cm and 5 cm from the free end of the pump tube.

If the optical fiber is guided to the end of the pump tube, light can be radiated e.g. directly into a Luer-lock connector with usually a transparent embodiment, from which said light is then emitted diffusely. Here, it is possible that the light source emits non-visible light, e.g. UV light, which is then converted into visible light by a conversion element, e.g. arranged at the tube connector, for example a phosphorus element, and emitted.

It can also be preferable for the second end of the optical fiber to be arranged in a recessed manner from the free end of the pump tube. As a result of the corresponding recessed arrangement of the second end of the optical fiber, it is possible to ensure that the second end of the optical fiber is arranged in the general field of view of the surgeon but, at the same time, it does not illuminate the actual operating region, even if the free end of the pump tube is guided into the operating region, for example for suctioning liquids away. The second end of the optical fiber can preferably be arranged 10 cm to 50 cm, more preferably 20 cm to 40 cm, from the free end of the pump tube.

It is preferable for the optical fiber to have one or more faults for light exit between the two ends thereof. Each fault is then perceivable to the surgeon as a point of light. Particularly in the case where more than one fault is provided, it is possible thus to ensure that at least one fault, and hence at least one point of light, lies in the general field of view of the surgeon, independently of the guidance of the pump tube in, or to, the operating region.

The faults are preferably embodied as notches on the outside of the optical fiber. If a plurality of faults are provided, it is preferable for the distance between the two faults adjacent to one another in each case to decrease along the pump tube toward the second end proceeding from the first end of the optical fiber. Thus, approximately the same amount of light can be output per unit length of the tube in the case of an otherwise suitable selection of the distances. If faults are present, the second end of the optical fiber can be free and thus serve as additional point of light. However, the second end of the optical fiber can alternatively also be covered such that only the faults serve as points of light.

The actuatable light source is preferably variable in color. Here, it is particularly preferable if the change in color of the light source can be controlled by the control unit. This can be achieved by movable color filters. However, it is particularly preferred if the light source comprises a plurality of illuminants with different colors which can be actuated individually in terms of the intensity thereof such that, overall, the desired color of the light source is set. The different colored illuminants preferably comprise the colors red, green and blue, and optionally white as well.

The actuatable light source preferably comprises light-emitting diodes (LEDs). LEDs are distinguished by the long service life thereof, even in the case of many switching on and off processes. Moreover, LEDs are also available in the colors red, green, blue and white, which are preferred for the adjustability by way of illuminants with different colors.

The control apparatus is preferably embodied to let the light source pulsate or blink depending on the flow rate set by the pump. In this context, "pulsating" means that the intensity of the light source varies rhythmically, but preferably without going out. "Blinking" means rhythmical switching on and off of the light source.

Furthermore, the control apparatus is preferably embodied to set the color of the light source in a manner dependent on the flow direction. As a result of this, it is possible to ensure that luminous points on pump tubes for the inflow shine with a different color than those on pump tubes for the outflow, said luminous points being e.g. perceivable at the faults and/or the second end of the optical fiber.

The pump apparatus preferably may also have one or more sensors for monitoring operating parameters of the pump unit and/or properties of the fluid to be pumped, such as e.g. the temperature thereof. The control apparatus is then preferably embodied to display the measured values of the sensor or sensors by way of the light source, with the color of the light source preferably being changed in a manner dependent on the measured values. By way of example, it is possible to measure the temperature of the fluid to be pumped and green can be set as color of the light source—to the extent that the temperature lies within a predetermined temperature range—, while the color of the light source is changed to red in the case of deviations of the temperature from the predetermined range. However, it is also possible for measured values or deviations of the measured values from intended values to be indicated by fast blinking of the illuminant or the like.

The optical fiber can be arranged on the outside of the pump tube. In so doing, the optical fiber can be fastened to the pump tube by e.g. adhesive bonding. It is also possible for the optical fiber to be coextruded with the pump tube. If the pump tube is at least partly transparent, the optical fiber can also be embedded into the pump tube.

The pump tube can also be a multi-lumen tube, preferably an at least partly transparent multi-lumen tube, with the optical fiber being guided through a chamber of the multi-lumen tube or being coextruded with the multi-lumen tube. In the remaining chambers of the multi-lumen tube, optical fibers for endoscopy illumination or laser applications, etc., can be guided next to a chamber for the liquid transport, for example.

The pump device is preferably a pump device for the rinsing liquid in the case of minimally invasive interventions by way of an endoscope, wherein the rinsing liquid is introduced into the operating region by way of the endoscope itself. To this end, the free end of the pump tube is preferably embodied for the connection to a corresponding endoscope. The invention also relates to a corresponding arrangement of such a pump unit according to the invention and such an endoscope, wherein the free end of the pump tube is connected to the endoscope. The explanations made above are referred to for the purposes of an explanation.

It is also possible for the actuatable light source not to be arranged at the pump unit, but instead to be arranged at the pump tube and to be connected to the control unit of the pump unit by way of an electric line which extends along the pump tube instead of the optical fiber. Here, the position of the light source on the pump tube can be selected as desired; however, it can be arranged, in particular, at the free end of the pump tube.

The invention is now described in an exemplary manner on the basis of advantageous embodiments, with reference being made to the attached drawings. In detail:

Figure 1:
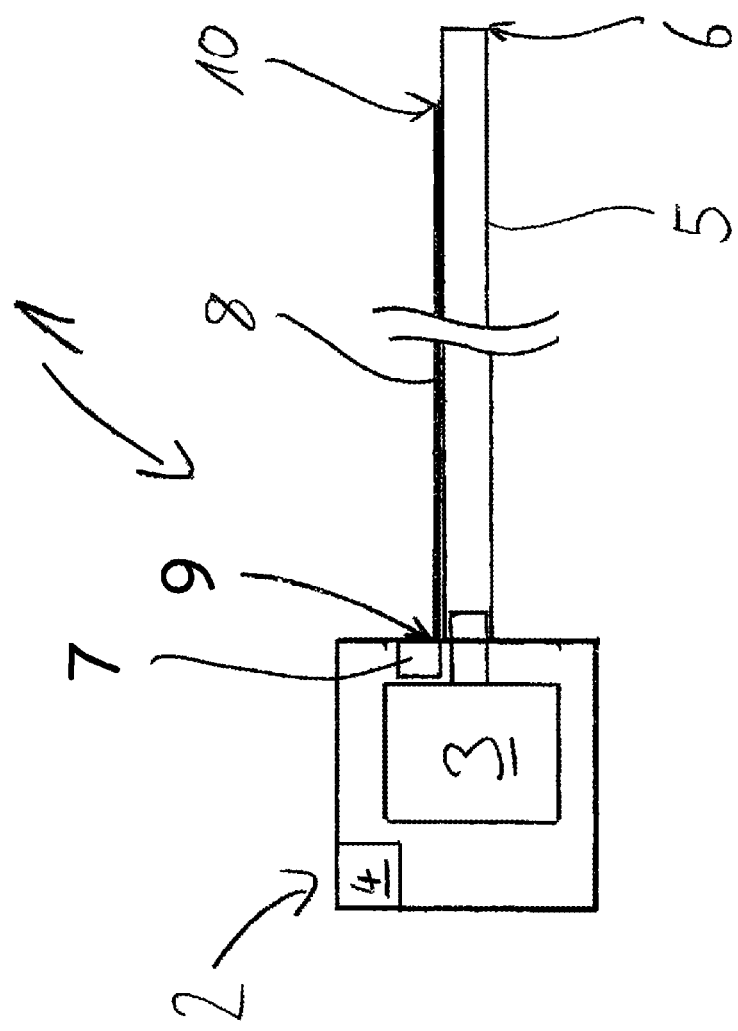
FIG. 1 shows a first exemplary embodiment of a pump device according to the invention.
Figure 2:
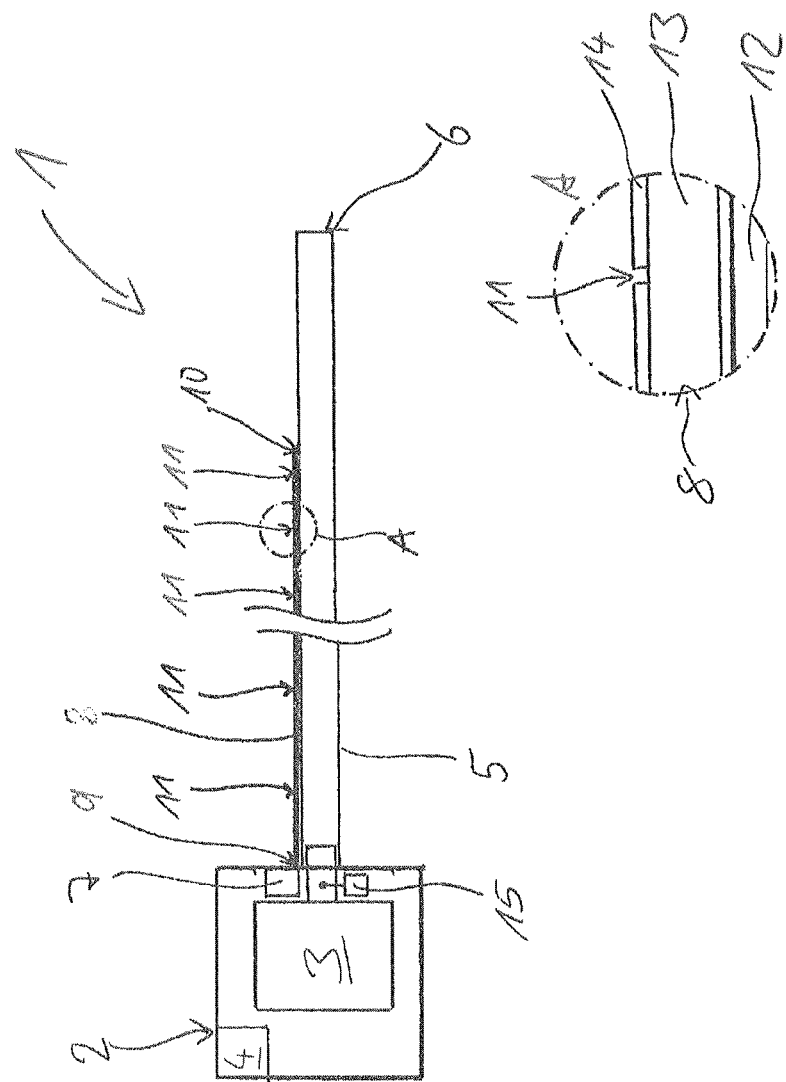
FIG. 2 shows a second exemplary embodiment of a pump device according to the invention.

FIGS. 3a-b show two exemplary embodiment variants of pump tubes for the pump devices in accordance with the FIGS. 1 and 2; and FIG. 4 shows a first exemplary embodiment of an arrangement according to the invention made of a pump device and an endoscope.

FIG. 1 schematically depicts a pump device 1 according to the invention, for use in operating theaters. The pump device 1 comprises a pump unit 2 with a pump 3 and a control unit 4. The pump 3 can be controlled by way of the control unit 4. To this end, operating elements (not depicted here) can also be present on the pump unit 2, by means of which the pump unit 2 can be actuated. By way of example, the desired flow rate of the pump 3 can be set by way of an appropriate operating element. However, the operating elements and all control lines are not depicted for reasons of clarity.

Connected to the pump unit 2 is a pump tube 5 such that fluids can be conveyed through the pump tube 5 by means of the pump 3 of the pump unit 2. Here, the pump 3 can e.g. convey rinsing liquid from a reservoir (not depicted here) through the pump tube 5 such that the rinsing liquid emerges at the free end 6 of the pump tube 5. It is also possible for the pump 3 of the pump unit 2 to work in the opposite direction such that a fluid at the free end 6 of the pump tube 5 is sucked in and conveyed through the pump tube 5 into a collection container (not depicted here).

Furthermore, a light source 7 is provided at the pump unit 2. The light source 7 is actuatable in terms of its switch-on state and in terms of the intensity thereof by means of the control unit 4.

The light source 7 can comprise a single illuminant, for example a light-emitting diode (LED). Alternatively, it is also possible for the light source to have a plurality of different colored, individually actuatable LEDs—in particular in red, green, blue and white—such that the light emitted by the light source 7 overall can additionally be set in terms of the color thereof by changing the intensity of the individual illuminants with different colors. In this case, the control unit 4 is embodied to control the color or the change in color of the light source 7.

An optical fiber 8 is provided along the pump tube 5.

With the first end 9 thereof, the optical fiber 8 is arranged in such a way that the light from the light source 7 is coupled into the optical fiber 8. The light coupled into the optical fiber 8 at the first end 9 reemerges at the second end 10 of the optical fiber 8 and it is perceivable there as a point of light. Here, the second end 10 of the optical fiber 8 is arranged at the free end 6 of the pump tube 5, more precisely 5 cm from the free end 6 of the pump tube 5.

The control unit 4 is embodied to control the light source 7 in a manner dependent on the operating state of the pump unit 2 and, in particular, of the pump 3. In particular, the light source 7 can be switched on and off in parallel with the switched on and off state of the pump 3. Furthermore, the control unit 4 can control the light source 7 in such a way that the light source 7 pulsates or blinks in a manner dependent on the flow rate set by the pump 3. Moreover, it is possible to change the flow direction of the fluid through the pump tube 5, which is determined by the pump direction of the pump 3, in the case of a color-changeable light source 7.

Since the free end 6 of the pump tube 5 is regularly brought into the actual operating region, or at least close thereto, in the case of pump devices 1 for operating theaters, as are depicted in FIG. 1, and since the second end 10 of the optical fiber 8 is arranged at this free end 6 of the pump tube 5, the surgeon obtains the corresponding information in the form of a point of light at the second end 10 of the optical fiber 8 in his field of view. This is because the point of light reproduces information about the operating state of the pump unit 2 due to the corresponding coupling-in of the light source 7. In particular—unlike in the prior art—it is no longer necessary for the surgeon to look away from the operating region, toward a display on the pump, or to question a person assisting in relation to the operating state of a pump in order to query the operating state of the pump unit 2.

FIG. 2 depicts a second exemplary embodiment of a pump device 1 according to the invention which, to a large extent, corresponds to the embodiment from FIG. 1. Therefore, only the differences of the exemplary embodiment in accordance with FIG. 2 in relation to the one from FIG. 1 are discussed in the following text. In relation to the rest, reference is made to the explanations above.

In the exemplary embodiment in accordance with FIG. 2, the optical fiber 8 is not guided up to the free end 6 of the pump tube 5. Rather, the second end 10 of the optical fiber is arranged recessed by 30 cm in relation to the free end 6 of the pump tube 5.

Moreover, the optical fiber 8 has a plurality of faults between the first end 9 and the second end 10 thereof, with the faults 11 being embodied for light exit. Thus, some of the light coupled-in at the first end 9 emerges at the faults 11, as a result of which each fault 11 is perceivable to the surgeon as a single point of light. Consequently, the surgeon can perceive a multiplicity of points of light along the pump tube 5, which each indicate the operating state of the pump unit 2.

The detailed illustration A in FIG. 2 shows the faults 11 in more detail. The optical fiber 8 arranged on the outside of the wall 12 of the pump tube 5 comprises a light-guiding core 13, which is surrounded by cladding 14. The cladding 14 has a lower refractive index than the light-guiding core 13 such that there is, as a matter of principle, total-internal reflection at the transition from the core 13 to the cladding 14. The optical fiber 8 has notches in the region of the faults 11, and so the cladding 14 is interrupted. Consequently, there no longer is total-internal reflection at the notches. Rather, light can escape from the light-guiding core 13 in the region of the fault 11. This light exit can be perceived by the surgeon as a point of light at the fault 11.

Proceeding from the first end 9 of the optical fiber, the distance between in each case two adjacent faults 11 decreases toward the second end 10 of the optical fiber. Here, proceeding from the pump unit 2, the largest distance is between the two closest faults 11, while the smallest distance is between the two faults 11 closest to the second end 10 of the optical fiber 8.

As a result of this measure, it is possible that approximately the same amount of light is emitted per unit length of the tube 5. Here, a person skilled in the art is readily able to suitably select the required individual distances between two adjacent faults 11 in order to obtain substantially the same intensity at all faults 11. The second end 10 of the optical fiber 3 is free in the exemplary embodiment in accordance with FIG. 2 and therefore it is likewise perceivable to the surgeon as a point of light.

In the exemplary embodiment in accordance with FIG. 2, the pump unit 2 furthermore has a temperature sensor 15, by means of which the temperature of the fluid conveyed through the pump tube 5 is measured. The control unit 4 has such an embodiment that the color of the light source 7 is changed in accordance with the measured values from the temperature sensor 15. By way of example, the color of the light source 7 can be green if the measured temperature moves within a predetermined temperature range. If the measured temperature lies outside of this temperature range, the color of the light source 7 can be changed toward red.

FIG. 3 depicts, in a schematic cross section, two embodiment variants of the pump tube 5 as are used in the device in accordance with the FIGS. 1, 2.

In the embodiment variant in accordance with FIG. 3*a*, the optical fiber 8 is arranged on the outside of the pump tube 5. Here, the optical fiber 8 can be retrospectively adhesively bonded to the pump tube 5. However, it is also possible that the optical fiber 8 is coextruded with the pump tube 5.

The pump tube 5 in accordance with FIG. 3*b* is embodied as a multi-lumen tube, with the optical fiber 8 being guided through one chamber of the multi-lumen tube. Here, the pump tube 5 is transparent, at least at the points at which light emerges from the optical fiber 8—i.e., at the second end 10 and/or at the faults 11. By way of example, optical fibers for endoscopy illumination or laser applications, etc., can be routed next to the central chamber for the fluid transport through the remaining chambers of the multi-lumen tube. The optical fiber 8 can be coextruded with the multi-lumen tube or it can be retrospectively introduced into an already available multi-lumen tube.

FIG. 4 depicts an arrangement according to the invention, made of a pump device 1 and an endoscope 20. Here, the pump device 1 corresponds to the one from FIG. 1, which is why reference is made to the explanations made there. In addition to the endoscope optics, the endoscope 20 has a supply channel for rinsing liquid, by means of which a cavity to be examined can be filled and rinsed. Corresponding endoscopes are known from the prior art.

The pump device 1 is embodied to supply rinsing fluid from a reservoir 21 in a corresponding arrangement. The operating state of the pump unit 2 of the pump device 1 is indicated to the surgeon by the point of light at the second end 10 of the optical fiber 8 in this case, said point of light being arranged close to the endoscope 20 due to the arrangement thereof at the end 6 of the pump tube 5 (cf. the explanations in relation to FIG. 1). Therefore, the surgeon obtains information about the operating state of the pump unit 2 in the direct vicinity of the operating region, and so he can perceive this information in passing and without difficulty.

The invention claimed is:

1. A pump device for use in operating theaters, comprising:
    a pump unit comprising:
        a pump,
        a control unit, and
        a light source actuatable by the control unit to display information about an operating state of the pump, and
    a pump tube connected to the pump unit and including an optical fiber extending along the pump tube, wherein:
- a first end of the optical fiber is arranged for coupling-in light from the actuatable light source;
- a second end of the optical fiber is recessed from a free end of the pump tube such that the second end of the optical fiber terminates proximally from the free end of the pump tube; and
- the free end of the pump tube is configured to be connected to an endoscope such that the second end of the optical fiber is spaced from a point of connection between the free end of the pump tube and the endoscope.

2. The device as claimed in claim 1, wherein the light source is embodied to output radiation outside of the visible range of light and provision is made of a conversion element for converting the radiation from the light source into visible light.

3. The device as claimed in claim 1, wherein the optical fiber has one or more faults for light exit between the first end and the second end of the optical fiber.

4. The device as claimed in claim 1, wherein the optical fiber has a plurality of faults for light exit between the first end and the second end of the optical fiber, and the faults are arranged such that a distance between a first pair of adjacent faults is smaller than a distance between a second pair of adjacent faults, the first pair of adjacent faults being positioned closer to the second end than the second pair of adjacent faults.

5. The device as claimed in claim 1, wherein the light source is variable in color, the control unit being embodied to control the color change of the light source.

6. The device as claimed in claim 5, wherein the control unit is embodied to change the color of the light source in a manner dependent on a flow direction of fluid through the pump tube.

7. The device as claimed in claim 1, wherein the control unit is embodied to control the light source to pulsate or blink depending on a flow rate of fluid through the pump tube.

8. The device as claimed in claim 1, wherein the pump has one or more sensors for monitoring operational parameters of the pump unit and/or properties of the fluid to be pumped, the control unit being embodied to display measured values from the one or more sensors by way of the light source.

9. The device as claimed in claim 1, wherein the optical fiber is arranged on an outer side of the pump tube, the optical fiber being adhesively bonded onto the pump tube or being coextruded with the latter, or the pump tube being a multi-lumen tube, with the optical fiber being guided through a chamber of the multi-lumen tube or being coextruded with the multi-lumen tube.

10. An arrangement comprising a pump device and an endoscope, wherein the pump device as claimed in claim 1, and the embodied endoscope are embodied to supply rinsing liquid into the operating region, wherein the free end of the pump tube is connected to the endoscope for supplying rinsing liquid.

* * * * *